United States Patent [19]

Koch et al.

[11] 4,148,898
[45] Apr. 10, 1979

[54] N-OXY-AJMALINE AND THE USE THEREOF IN TREATING CARDIOVASCULAR DISORDERS

[75] Inventors: Michel G. Koch, Montfermeil; Jacques M. Peyroux, Paris, both of France

[73] Assignee: Societe d'Etudes et de Recherches Enzymologiques et pharmacologiques - Enzypha, Paris, France

[21] Appl. No.: 882,446

[22] Filed: Mar. 1, 1978

[30] Foreign Application Priority Data

Mar. 16, 1977 [FR] France .................................. 77 07842

[51] Int. Cl.² .................. A61K 31/445; C07D 471/08
[52] U.S. Cl. .................................... 424/256; 424/262; 546/40
[58] Field of Search ...................... 260/293.53, 293.55; 424/262, 256

[56] References Cited

PUBLICATIONS

Merlini, L. et al., Tetrahedron, 28, 5971–5975 (1972).

Pelletier, S. (Editor), Chemistry of the Alkaloids, van Nostrand Reinhold, New York, 1970, pp. 218–219.

*Primary Examiner*—Natalie Trousof
*Assistant Examiner*—Richard A. Schwartz
*Attorney, Agent, or Firm*—Roylance, Abrams, Berdo & Farley

[57] ABSTRACT

N-oxy-ajmaline of the formula

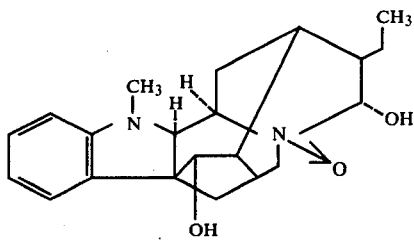

useful for treating myocardium infarct and ventricular and supraventricular tachycardia.

2 Claims, No Drawings

N-OXY-AJMALINE AND THE USE THEREOF IN TREATING CARDIOVASCULAR DISORDERS

The present invention has as its aim a novel compound, named N-oxy-ajmaline, the method of preparing it and its application in therapeutics.

N-oxy-ajmaline of the invention corresponds to formula I:

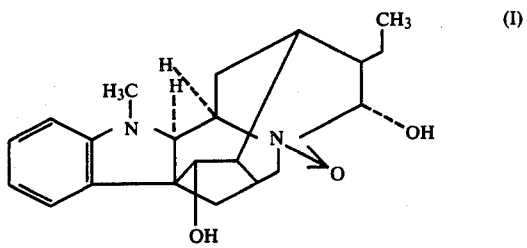

The method of the invention consists in oxidising ajmaline of formula II:

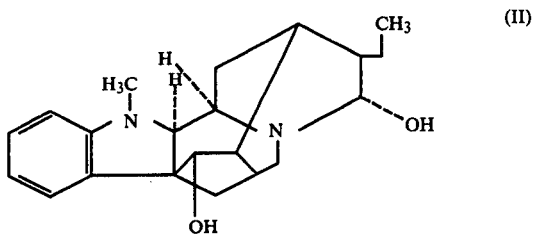

The oxidising agent used in this method may be indifferently a peroxide such as hydrogen peroxide, or a peracid, such as metachloroperbenzoic acid.

The following preparations are given by way of example to illustrate the invention.

EXAMPLE 1: N-oxy-ajmaline 10 g of ajmaline were put into suspension, with stirring, in 135 cm$^3$ of 96° ethanol. 15 cm$^3$ of 110 volumes hydrogen peroxide were progressively added. The medium became progressively soluble. If the solubilization was not complete after half an hour, a few drops of hydrogen peroxide were progressively added until total dissolution was obtained. The stirring was continued for about 1 to 3 hours then, possibly after filtering, the solution was left at ordinary temperature for a few days (about 4 days).

There gradually formed a crystalline precipitate of N-oxy-ajmaline.

The crystals were collected and washed with a little ethanol, then abundantly with ether (6 to 10 times).

Then, the crystals were dried in a phosphoric vacuum for 24 to 48 hours at the ordinary temperature then by progressively raising the temperature to 80°–100° C. until constant weight was obtained.

9.650 g of crystals were obtained.

The concentrated mother lye gives also crystals which were treated as above. 0.250 g of crystals are obtained. The total amount of the obtained crystals was 9.9 g.

Yield: 94%
Melting point: 168°–170° C.
Empirical formula: $C_{20}H_{26}O_3N_2$
Mass spectrum: m/e 342 (M+)

Treated with iron filings, in solution in diluted acetic acid (50/50), the N-oxy-ajmaline is reduced to ajmaline.

EXAMPLE 2

200 mg of ajmaline were put in solution in an organic solvent such as chloroform or a mixture of chloroform and methanol (5 ml). A solution of 200 mg of metachloroperbenzoic acid in 5 ml of the same solvent was slowly added, with stirring, the mixture being cooled in ice. The kinetics of the reaction were followed by thin layer chromatography (alkaline Kieselgel plate; solvent CHCl$_3$ 90-MeOH 10). At the same time as the N-oxyajmaline, there were formed more polar secondary products, already in a important amount whereas the whole of the ajmaline was not yet transformed. The solution was diluted with chloroform, washed with an 15% aqueous solution of KHCO$_3$, dried, filtered and dry distilled. The residue obtained, chromatographed on a silica column of activity V, gave 104 mg of N-oxyajmaline (Yield 49.5%).

The compound of formula I was tested on laboratory animals and showed antidysrythmic properties, a good cardiac tolerance and very low toxicity.

1. Antidysrythmic properties

They were demonstrated in mice on the fibrillations induced by inhaling chloroform (Lawson's test) and in dogs on the arythmia caused by ligature of a coronary artery and the tachycardia induced by ouabain.

Lawson's Test

The protocol followed is that proposed by Vargaftig and Coignet (Eur. J. Pharmacol. 1969, 6, 49).

Conventional female mice (18–20 g) are used divided randomly into batches of 20 animals. The products were administered intraperitoneally (0.4 ml/20 g) 2 minutes before inhaling chloroform. A thoracotomy practised as soon as breathing stopped allowed the presence or absence of fibrillations to be ascertained.

In these conditions the effective doses 50 of two reference compounds, i.e. quinidine (successively tested doses: 15, 30 and 60 mg/kg) and ajmaline hydrochloride (10, 20 and 40 mg/kg) as well as the compound of the invention (20, 40 and 80 mg/kg).

The results are shown in Table I below.

TABLE I

| Compounds tested | ED 50 and fiducial limits* in mg/kg (p = 0.05) | |
|---|---|---|
| Qunidine | 23 | (16.4 – 32.2) |
| Ajmaline (hydrochloride) | 21 | (13.1 – 33.6) |
| Compound of the inventon | 29 | (18.1 – 46.4) |

*According to Lichfield and Wicoxon

Arythmia by ligature of a coronary artery in dogs

A single time ligature technique according to the protocol proposed by Cosnier and Grimal (J. Pharmacol. 1973, 4, 273-8) was used. The test was carried out on 11 bastard dogs of a weight between 8 and 17 kg.

A compound reference, ajmaline hydrochloride (commercial name: Cardiorythmine R) and the compound of the invention were tested in this way. They were administered by slow perfusion (10 mins), the first in doses of 3 and 6 mg/kg and the second in doses of 5, 10 and 30 mg/kg.

The number of sinusal complexes was counted at times 2, 5, 10 minutes after perfusion over two one-minute periods with one minute interval and at times of 15, 30, 45 and 60 minutes over three one-minute periods still with a one minute interval.

There was thus determined the percentage increase in the number of complexes and the activity of the products is evaluated according to an arbitrary table inspired by the one proposed by Cosnier and Grimal.

0 from 0 to 10% increase in relation to the control measurement made before administration of the product.
0.5 from 10 to 50% increase
1 more than 50% increase
1.5 more than 50% increase with a period of at least one minute greater than 90%
2 pure sinsual rhythm for at least one minute.

The results are given in tables II and III following:

TABLE II:

| | ajmaline hydrochloride | |
|---|---|---|
| | Activity with doses of | |
| DOG N° | 3 mg/kg | 6 mg/kg |
| 1 | 1.5 | |
| 2 | 0.5 | 1 |
| 3 | 0 | 0.5 |
| 4 | 1.5 | |
| Total | 3.5 | 1.5 |
| theoritical maximum | 8 | 4 |

TABLE III:

| | Compound of the invention | | |
|---|---|---|---|
| | Activity with doses of | | |
| DOG N° | 5 mg/kg | 10 mg/kg | 30 mg/kg |
| 5 | 1 | | |
| 6 | 0 | 0.5 | 1 |
| 7 | 0 | 0 | |
| 8 | 1 | 1.5 | |
| 9 | 0.5 | 0 | 1 |
| 10 | 0 | 0 | 1 |
| 11 | 1.5 | 1 | |
| Total | 4 | 3 | 3 |
| theoretical maximum | 14 | 12 | 6 |

Ouabain ventricular tachycardia in dogs

This property was studied by using LUCCHESI's technique (J.P.E.T. 1965, 148, 94–99) according to the protocole proposed by GIUDICELLI (J. Pharmacol. Paris, 1973, 4, 139–142).

The test was carried out on 15 bastard dogs of both sexes of a weight between 8 and 15 kg.

The animals were anaesthetized with Nembutal (35 mg/kg/i.v.), the products were injected intravenously and ouabain was administered in an aqueous solution.

Once the tachycardia was established, the products to be tested were perfused in solution in the physiological solute at the rate of 1 mg/kg per ml and per minute of the compound of the invention, and 1 mg/kg or two ml and per minute for the comparison compound, chloracetyl ajmaline.

The results obtained are given in Table III' below. It can be seen that the compound of the invention has an activity as high as that of ajmaline chloracetyl.

2. Cardiac Tolerance

A study of the recording of ECG shows that the first modification observed on the plot during perfusion is a lengthening out of the P.R. space and a reduction of the cardiac frequency. The development of these two parameters were followed in time. The results are shown in tables IV and V below.

TABLE III

| Compound tested | Number of animals | | | Dose in γ/kg of oubain causing tachycardia m ± s m | Dose in mg/kg causing return to a sinusal rhythm for 30 mins. m ± s m |
|---|---|---|---|---|---|
| | Total | Taken into account | Protected | | |
| Compound of the invention | 8 | 6 | 5 | 74.00 ± 4.97 | 12.8 ± 2.96 |
| Chloracetyl Ajmaline | 7 | 7 | 5 | 75.00 ± 5.69 | 12.6 ± 3.97 |

TABLE IV:

Increase in PR space
(calculated on the average of the results obtained, as an absolute value in relation to the initial value and expressed in 1/1000 second.)

| | Ajmaline (hydrochloride) | | Chloroacetyl ajmaline | Compound of the invention |
|---|---|---|---|---|
| Time in minutes | 2.5 mg/kg/min. | 5 mg/kg/min. | 5 mg/kg/min. | 20 mg/kg/min. |
| 0.5 | 3.4 | 10 | 2.5 | 2 |
| 1 | 17.6 | 18 | 5 | 2.5 |
| 2 | 24.2 | 27 | 7.5 | 4 |
| 3 | 28.6 | 30 | 16.6 | 8 |
| 4 | 30.4 | 37 | 20 | 9 |
| 5 | 35.4 | 47 | 18 | 12.5 |
| 6 | 40.4 | 57 | 24 | 17 |
| 7 | 33.6 | 67 | 22.5 | 23 |
| 8 | 33.6 | 67 | 26 | 28 |
| 9 | 42.2 | 67 | 24 | 30 |
| 10 | 43 | 77 | 26 | 30 |
| 12 | 48.6 | | 30 | 33 |
| 14 | 52.6 | | 35 | 38 |
| 16 | 57.6 | | | 40 |
| 18 | 59.6 | | | 47 |
| 20 | 62.6 | | | |
| 22 | 65.6 | | | |

TABLE V:

Reduction in the cardiac frequency
(calculated on the average of the results obtained,
as an absolute value,
in relation to the initial value
and expressed in beats per minute)

| Time in minutes | Ajmaline (hydrochloride) 2.5 mg/kg/min. | Ajmaline (hydrochloride) 5 mg/kg/min. | Chloroacetyl ajmaline 5 mg/kg/min. | Compound of the invention 20 mg/kg/min. |
| --- | --- | --- | --- | --- |
| 0.5 | 12 | 33 | 15 | 20 |
| 1 | 16 | 55 | 30 | 28 |
| 2 | 22 | 74 | 42 | 40 |
| 3 | 12 | 78 | 55 | 48 |
| 4 | 24 | 83 | 57 | 61 |
| 5 | 20 | 133 | 55 | 62 |
| 6 | 38 | 182 | 55 | 72 |
| 7 | 36 | 193 | 57 | 88 |
| 8 | 53 | 160 | 59 | 99 |
| 9 | 56 | 183 | 57 | 110 |
| 10 | 68 | 208 | 58 | 116 |
| 12 | 98 | | 67 | 133 |
| 14 | 88 | | 72 | 151 |
| 16 | 118 | | 77 | 162 |
| 18 | 133 | | | 175 |
| 20 | 153 | | | |
| 22 | 183 | | | |

3. Acute toxicity

The toxicity was determined in mice by oral way (LD 50) and on rats by slow perfusion (minimum lethal dose).

Determination of LD 50 P.O. with mice

The acute toxicity of the compound of the invention was determined per os on batches of 10 male mice and 10 female mice of the Swiss EOPS, in comparison with ajmaline hydrochloride.

Mortality was taken 7 days after administration and no delayed mortality was observed.

The results are given in table VI

TABLE VI

| Compounds | DL 50 and fiducial limits in mg/kg ($p = 0.5$)* male | female |
| --- | --- | --- |
| of the invention | >3400 | >3400 |
| ajmaline hydro-chloride | 500 (381–656) | 560 (425–736) |

*Determined by the method of Litchfield and Wilcoxon (J. Pharmacol. 1949, 96, 99–119)

Determination of the minimum lethal dose (DMM) on rats

The DMM was determined on female EOPS rats. The animals of a weight between 350 and 400 g were anaesthetized with urethane (1.25 g/kg). The substances in solution in the physiological solute were perfused at the rate of 0.5 ml per min. in the jugular vein. The electrocardiogram was recorded with DII deviation.

The effets of the compound of the invention (20 mg/kg/minute) were compared with those of ajmaline hydrochloride (2.5 and 5 mg/kg/minute) and chloro-2-acetyl-ajmaline hydrochloride (5 mg/kg/minute).

The results are given in table VII below.

TABLE VII:

| Product | Minimum lethal dose Doses in mg/kg/minute | Number of animals per batch | DMM in mg/kg m ± sm |
| --- | --- | --- | --- |
| Ajmaline chlorhydride | 2.5 | 6 | 65.3 ± 2.70 |
| | 5 | 6 | 66.5 ± 11.3 |
| Chloracetyl ajmaline (hydrochloride) | 5 | 6 | 119.6 ± 18 |
| Compound of the invention | 20 | 6 | 476 ± 51.3 |

Tables VI and VII show then the low toxicity of the compound of the invention.

N-oxy-ajmaline is indicated in the treatment of myocardium infarct and ventricular and supraventricular tachycardia troubles.

It will be administred orally in the form of tablets, troches or capsules (1 to 1.5 g of active ingredient per day in 4 to 6 doses) or intravenously (150 to 200 mg of active ingredient per day in 2 to 3 slow injections).

What is claimed is:

1. N-oxy ajmaline of the formula:

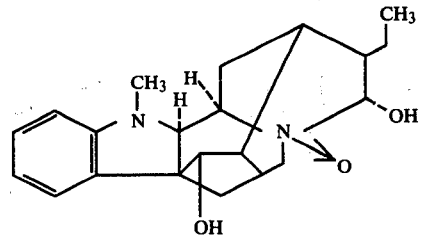

2. A method for the treatment of myocardium infarct and ventricular and supraventricular tachycardia troubles which comprises administering to a host subject afflicted with said troubles a therapeutically effective amount of the compound of claim 1.

* * * * *